(12) United States Patent
Constantine et al.

(10) Patent No.: US 10,799,438 B2
(45) Date of Patent: Oct. 13, 2020

(54) SOLID EFFERVESCENT HAIR CONDITIONING COMPOSITION

(71) Applicant: COSMETIC WARRIORS LIMITED, Poole, Dorset (GB)

(72) Inventors: Mark Constantine, Poole (GB); Margaret Joan Constantine, Poole (GB); Helen Elizabeth Ambrosen, Wimborne (GB); Rowena Jacqueline Bird, Christchurch (GB); Daniel James Campbell, Poole (GB)

(73) Assignee: COSMETIC WARRIORS LIMITED, Poole, Dorset (GB)

( * ) Notice: Subject to any disclaimer, the term of this patent is extended or adjusted under 35 U.S.C. 154(b) by 0 days.

(21) Appl. No.: 15/568,438

(22) PCT Filed: Apr. 21, 2016

(86) PCT No.: PCT/GB2016/051104
§ 371 (c)(1),
(2) Date: Oct. 20, 2017

(87) PCT Pub. No.: WO2016/170338
PCT Pub. Date: Oct. 27, 2016

(65) Prior Publication Data
US 2018/0110702 A1    Apr. 26, 2018

(30) Foreign Application Priority Data
Apr. 22, 2015 (GB) .................................. 1506830.7

(51) Int. Cl.
| | | |
|---|---|---|
| *A61K 8/19* | (2006.01) |
| *A61Q 5/12* | (2006.01) |
| *A61K 8/02* | (2006.01) |
| *A61K 8/34* | (2006.01) |
| *A61K 8/46* | (2006.01) |
| *A61K 8/92* | (2006.01) |

(52) U.S. Cl.
CPC ............. *A61K 8/19* (2013.01); *A61K 8/0216* (2013.01); *A61K 8/342* (2013.01); *A61K 8/463* (2013.01); *A61K 8/922* (2013.01); *A61Q 5/12* (2013.01); *A61K 2800/222* (2013.01)

(58) Field of Classification Search
CPC .... A61K 8/8147; A61K 8/8152; A61K 8/894; A61K 2800/222; A61K 2800/42; A61K 8/22; A61K 8/27; A61K 8/46; A61K 8/4933; A61K 8/817; A61K 8/86; A61K 9/06; A61K 8/375; A61K 8/39; A61Q 19/10; A61Q 5/006; A61Q 5/08; A61Q 5/12; A61Q 9/04

See application file for complete search history.

(56) References Cited

U.S. PATENT DOCUMENTS

| | | | | |
|---|---|---|---|---|
| 5,824,629 A * | 10/1998 | Petritsch | ............. | A61K 8/0216 510/120 |
| 5,955,057 A | 9/1999 | Maunder et al. | | |
| 6,121,215 A | 9/2000 | Rau | | |
| 8,574,561 B1 * | 11/2013 | Patel | ........................ | A61K 8/27 424/401 |
| 2003/0165454 A1 * | 9/2003 | Snyder | ................ | A61K 8/8147 424/70.16 |
| 2004/0126411 A1 * | 7/2004 | Lagatol | ................ | A61K 8/0208 424/443 |
| 2005/0042262 A1 * | 2/2005 | Hasenoehrl | .......... | A61K 8/0208 424/443 |
| 2005/0123573 A1 * | 6/2005 | Spadini | .............. | C11D 17/0004 424/401 |

FOREIGN PATENT DOCUMENTS

| | | | |
|---|---|---|---|
| DE | 19745964 A1 | 6/1998 | |
| EP | 2316414 A1 | 5/2011 | |
| GB | 2383950 A * | 11/2002 | ............. A61K 7/075 |
| GB | 2383950 A1 | 7/2003 | |
| GB | 2016/051104 | 6/2016 | |
| JP | 61-37718 A | 2/1986 | |
| JP | 62-294604 A | 12/1987 | |
| JP | 63-135317 A | 6/1988 | |
| JP | H04-501422 A1 | 3/1992 | |
| JP | H10-501235 A | 2/1998 | |
| JP | 2009-029829 A | 2/2009 | |
| JP | 2013-253056 A | 12/2013 | |
| JP | 2015-124176 A | 7/2015 | |
| JP | 2016-507562 A | 3/2016 | |
| RU | 2314789 C2 | 1/2008 | |
| RU | 2436564 C2 | 11/2009 | |
| RU | 2464012 C1 | 10/2012 | |
| WO | 89/03670 A1 | 5/1989 | |
| WO | 90/14070 A1 | 11/1990 | |
| WO | 95/33446 A | 12/1995 | |
| WO | 00/57858 A1 | 10/2000 | |
| WO | 03/057182 A1 | 7/2003 | |
| WO | 2003/094873 A1 | 11/2003 | |
| WO | 2007/038733 A1 | 4/2007 | |
| WO | 2009/147380 A1 | 12/2009 | |
| WO | 2010/016591 A1 | 2/2010 | |
| WO | 2011/115227 A1 | 9/2011 | |
| WO | 2014/124067 A1 | 8/2014 | |

OTHER PUBLICATIONS

International Search Report and Written Opinion for PCT/GB2016/051104, dated Jun. 20, 2016.
Search Report for British Patent Application No. 1506830.7, dated Jan. 27, 2016.
Office Action for Russian Patent Application No. 2017 140 470, dated Apr. 8, 2019.
Office Action for Russian Patent Application No. 2017 140 470, dated Nov. 11, 2019.

(Continued)

*Primary Examiner* — Audrea B Coniglio
(74) *Attorney, Agent, or Firm* — Merchant & Gould P.C.

(57) ABSTRACT

A solid hair conditioner composition includes (i) a hair conditioner concentrate; and (ii) a carbon dioxide effervescing system including a salt of carbonic acid and an acidifying agent.

22 Claims, No Drawings

(56) References Cited

OTHER PUBLICATIONS

Japanesestuffchannel, posted Feb. 4, 2015, "ASMR Prize Bath Bomb #164 Lollipop", YouTube, [Online], Available from https://www.youtube.com/watch?v=0_XS9JXtdMA. [Accessed Nov. 14, 2019].
Examination Report under Section 18(3) for British Patent Application No. 1506830.7, dated Nov. 15, 2019.

* cited by examiner

SOLID EFFERVESCENT HAIR CONDITIONING COMPOSITION

This application is a National Stage of PCT/GB2016/051104, filed 21 Apr. 2016, which claims benefit of British Patent Application No. 1506830.7, filed 22 Apr. 2015 which applications are incorporated herein by reference. To the extent appropriate, a claim of priority is made to each of the above disclosed applications.

FIELD OF THE INVENTION

The present invention relates to a solid hair conditioning concentrate, a process for producing said hair conditioning concentrate, and a product prepared by the method.

BACKGROUND TO THE INVENTION

Whilst shampoos typically contain anionic surfactants, which act to reduce the surface tension of water and remove oil and dirt that naturally build up on strands of hair, an accumulation of static energy can arise as hair strands naturally carry an anionic charge, due to the high proportion of cysteine amino acids present in the cuticle proteins.

Hair conditioners are popular cosmetic products used to address the problem of oil, dirt and static build up on the hair. It is known by those skilled in the art that conditioners often contain antistatic agents, such as behenzyl trimethyl ammonium chloride, cationic guar gum, cetrimonium bromide and other quaternary cationic surfactants. The positively charged nature of these materials allow them to interact with the negative charge present in the hair cuticle, helping the cuticles to lie flat giving a smooth finish to the hair.

However when using these anti-static agents it is important that they do not accumulate on the hair, as this can leave it lank and flat. By using an emulsifying wax in combination with a surfactant, such as cetearyl alcohol & sodium lauryl sulfate, sodium polynaphthalenesulfonate or stearamidopropyl dimethylamine the mechanism of removing excess charge from the hair is facilitated.

Conditioning systems often combine this antistatic component with an emulsifying/surfactant wax in order to remove any excess antistatic materials, which are typically oil based. In order to ensure the motility of the product, conditioners are commonly formulated as emulsions, so that the product can be easily applied to wet hair and to ensure effective distribution. Using a water phase and an oil phase within the conditioner formulation gives one skilled in the art the opportunity to utilise other materials to elicit different effects on the hair.

The specific effect a conditioner has on a user's hair is determined by the proportion of surfactant/emulsifying wax in relation to the amount of antistatic agent. Deep or intensive conditioners, typically applied to dry, damaged or thicker hair, will contain more antistatic agents and more surfactant/emulsifying wax, to prompt the build up of a cationic residue on the hair; thereby helping the cuticle lay flatter than would normally be possible with standard conditioning. Protein conditioners usually contain keratin, or a protein derivative, and typically possess the same effects as the deep or intensive conditioners. The protein component of the conditioner is able to coat the hair strand, due to the effect exhibited by the anti-static agent, in turn strengthening the hair strand. Leave-in conditioners do not contain a surfactant/emulsifying wax, as it is a desired affect to allow the anti-static agent to build up on the hair, encouraging the hair cuticles to lie flat and produce a smooth finish to the hair.

Pre-shampoo conditioning treatments have grown in popularity. They moisturise and repair the cortex of the hair, thereby improving the condition of the hair and scalp, whilst providing protecting against the adverse effects of colouring and styling.

Healthy hair stretches when wet before returning to its original length when dry, however hair in poor condition snaps and breaks when stretched. The key to this is the cortex of the hair, which provides strength, colour and texture. Without a moisture rich and softened cortex the hair becomes thin, frizzy and far more prone to damage and breakage. Furthermore a damaged cortex may result in the degeneration of the cuticle, which is the outermost layer that protects the cortex. By moisturising and softening the cuticle one skilled in the art will understand that suppleness, elasticity will be restored without weighing down or coating the hair.

As conditioner formulations have evolved, a greater focus has been put on increasing the profitability of the product, in one instance by increasing the water content, which can often compromise the effectiveness of the conditioner. Users are aware of this increase in water content or at least are aware of the reduced effectiveness of the product. Therefore there is a strong demand for "salon grade" conditioners, in which a high quality and intensely nourishing conditioner is applied to the hair. This conditioner is typically a combination of conditioning components compounded in a hair salon and tailored to the specific requirements of the hair type. The preparation of such freshly prepared conditioners is time-consuming, may require skill to correctly determine the proportions of the conditioner components or at least the proportion of conditioning components to water and may create a significant amount of mess in its preparation.

The present invention seeks to provide a solid hair conditioner composition that addresses the problems of the prior art.

SUMMARY OF THE INVENTION

In a one aspect there is provided a solid hair conditioner composition comprising
 (i) a hair conditioner concentrate; and
 (ii) a carbon dioxide effervescing system comprising a salt of carbonic acid and an acidifying agent.

In a one aspect there is provided a unit dose of a solid cosmetic composition, wherein the unit dose comprises
 (a) a solid hair conditioner composition in a predetermined amount
 (b) a stirring device for stirring a liquid
 wherein the stirring device is partially embedded within the solid cosmetic composition.

In a one aspect there is provided a process for the production of a solid hair conditioner composition comprising
 (i) a hair conditioner concentrate; and
 (ii) a carbon dioxide effervescing system comprising a salt of carbonic acid and an acidifying agent.
 the process comprising the steps of
 (a) when the hair conditioner concentrate or components thereof is solid, heating the hair conditioner concentrate or components thereof to provide a liquid,
 (b) mixing the carbon dioxide effervescing system with the liquid hair conditioner concentrate, (c) cooling the mixture to provide the solid hair conditioner composition in a predefined solid shape.

In a one aspect there is provided use of a carbon dioxide effervescing system comprising a salt of carbonic acid and an acidifying agent for dispersing a solid hair conditioner composition in water.

In a one aspect there is provided a method of preparing a hair conditioner composition comprising the step of contacting water and a solid hair conditioner composition comprising (i) a hair conditioner concentrate; and
(ii) a carbon dioxide effervescing system comprising a salt of carbonic acid and an acidifying agent.

The present invention provides a solid hair conditioning composition which by virtue of a solid nature does not require packaging and therefore offers numerous environmental advantages, such as reduction of waste product and packaging and reduced environmental impact attributable to transportation of the concentrated composition. Furthermore, because the end user contacts the solid hair conditioner composition with water to form a hair conditioner which is to be used shortly afterwards, the end user has a "salon style" experience of applying a high quality and freshly made conditioner to their hair. Yet further, by providing a composition which does not require the high quantities of water used in the prior art compositions, a system is provided which may be free of the preservatives necessary in high water content systems.

The above advantages are achieved by providing the hair conditioner in a concentrated form and combining it with a carbon dioxide effervescing system. By the provision of this combination of components, in use, the hair conditioning composition may be combined with water, and in particular warm water. When contacted with water the carbon dioxide effervescent system generates carbon dioxide. This in situ generation of carbon dioxide disperses the hair conditioner concentrate within the water. More particularly the carbon dioxide generation results in a final hair conditioner in to which a large quantity of water may be incorporated. The carbon dioxide generation ensures a complete and even distribution of the hair conditioner concentrate within the water and this is achieved without the need for extensive or vigorous stirring during preparation. For example, the essential use of a mixer or a blender is avoided. This is desirable because of the cleaning of the mixer or blender after the preparation of the conditioner that would otherwise be required. Therefore, to prepare a salon type hair conditioner the user need only provide a container holding a small amount of water into which the solid hair conditioner composition is placed. This may be then stirred gently to assist in bringing water into contact with the carbon dioxide generating system and to assist with the dispersion of the hair conditioner concentrate. After a short period the hair conditioner is ready for use and after use only the container and possibly the stirrer requires cleaning.

For ease of reference, these and further aspects of the present invention are now discussed under appropriate section headings. However, the teachings under each section are not necessarily limited to each particular section.

DETAILED DESCRIPTION

Composition

As discussed herein, in one aspect of the present invention, there is provided a solid hair conditioner composition comprising (i) a hair conditioner concentrate; and
(ii) a carbon dioxide effervescing system comprising a salt of carbonic acid and an acidifying agent.

As discussed herein, the hair conditioner composition is a solid. Solid products of the present invention are compositions which can substantially sustain their physical shape when unsupported by external means, e.g. packaging etc. Thus, they are considered to be solid, solid like, in solid form or in solid-like form at room temperature. For the avoidance of doubt the solid product must remain substantially solid at up to 30° C.

By solid-like, it is understood that some materials are considered to be solid, yet over an extremely long period of time, may alter in shape, e.g. amorphous materials such as glass etc. However, they are considered to be solid-like as, for the purpose they fulfil, they are solid. The solid form of the solid compositions of the present invention means that external packaging is not required to maintain the shape of the composition.

Hair Conditioner Concentrate

As discussed herein, in the solid hair conditioner composition of the present invention contains a hair conditioner concentrate. The hair conditioner concentrate may be present in any suitable amount to provide the necessary properties of the final product. In one aspect the hair conditioner concentrate is present in an amount of at least 20% by weight of the solid hair conditioner composition. In one aspect the hair conditioner concentrate is present in an amount of at least 30% by weight of the solid hair conditioner composition. In one aspect the hair conditioner concentrate is present in an amount of at least 40% by weight of the solid hair conditioner composition. In one aspect the hair conditioner concentrate is present in an amount of at least 50% by weight of the solid hair conditioner composition.

In one aspect the hair conditioner concentrate is present in an amount of no greater than 95% by weight of the solid hair conditioner composition. In one aspect the hair conditioner concentrate is present in an amount of no greater than 90% by weight of the solid hair conditioner composition. In one aspect the hair conditioner concentrate is present in an amount of no greater than 85% by weight of the solid hair conditioner composition. In one aspect the hair conditioner concentrate is present in an amount of no greater than 80% by weight of the solid hair conditioner composition. In one aspect the hair conditioner concentrate is present in an amount of no greater than 75% by weight of the solid hair conditioner composition. In one aspect the hair conditioner concentrate is present in an amount of no greater than 70% by weight of the solid hair conditioner composition. In one aspect the hair conditioner concentrate is present in an amount of no greater than 65% by weight of the solid hair conditioner composition.

In one aspect the hair conditioner concentrate is present in an amount of from 40 to 70% by weight of the solid hair conditioner composition. On one aspect the hair conditioner concentrate is present in an amount of from 50 to 65% by weight of the solid hair conditioner composition.

Hair conditioner concentrates are known to those skilled in the art and are materials and compositions which condition the hair.

As the skilled person will appreciate, a hair cleansing composition differs from a hair conditioner composition or a hair conditioner concentrate. A hair cleansing composition (more commonly referred to as shampoos) typically contains surfactants that emulsify excess sebum and impurities from the hair, so that they can be washed away by the bathing water. Whilst sebum is beneficial for the condition of the hair, excess sebum gives rise to the effect of 'greasy' hair. Anionic surfactants are often used to remove excess sebum, although they can also cause the hair to become dry and brittle, without any additional conditioning. Hair cleansing compositions may also be able to provide anionic charges to the hair strands, which may volumise the hair.

In contrast, and as the skilled person will appreciate, the primary function of a hair conditioner is typically to neutralise the residual anionic charge present on the hair strands by delivering a positively charged component to the hair, thus flattening and smoothing the cuticles.

In one aspect the hair conditioner concentrate is selected from emulsifying waxes, sodium polynaphthalene sulfonate, stearamidopropyl dimethylamine (aka N-[3-(dimethylamino) propyl]octadecanamide) and mixtures thereof.

The selection of emulsifying waxes as the hair conditioner concentrate is particularly preferred. The emulsifying wax may be selected from cetearyl alcohol (aka cetostearyl alcohol or cetylstearyl alcohol), stearic acid, glyceryl stearate, a combination of cetearyl alcohol and sodium lauryl sulphate (SLS), and mixtures thereof. The emulsifying wax in one aspect is a combination of cetearyl alcohol and sodium lauryl sulphate. Thus in one aspect the hair conditioner concentrate is a combination of cetearyl alcohol and sodium lauryl sulphate.

In a preferred aspect, the hair conditioner composition is a wash-out conditioner such that the user may wash the composition out of their hair after use.

When the hair conditioner concentrate is a combination of cetearyl alcohol and sodium lauryl sulphate, the cetearyl alcohol and sodium lauryl sulphate may be present in any suitable amount relative to each other. In one aspect the cetearyl alcohol and sodium lauryl sulphate are present in a ratio of from 20:1 to 2:1 by weight. In a further aspect the cetearyl alcohol and soldium lauryl sulphate are present in a ratio of from 20:1 to 4:1. In a further aspect the cetearyl alcohol and sodium lauryl sulphate are present in a ratio of from 20:1 to 5:1 by weight. In a further aspect the cetearyl alcohol and sodium lauryl sulphate are present in a ratio of from 12:1 to 8:1 by weight.

When the hair conditioner concentrate is a combination of cetearyl alcohol and sodium lauryl sulphate, the cetearyl alcohol may be present in an amount of 65 to 95 wt. % based on the combined amount of cetearyl alcohol and sodium lauryl sulphate, such as from 70 to 90 wt. % based on the combined amount of cetearyl alcohol and sodium lauryl sulphate, such as from 75 to 85 wt. % based on the combined amount of cetearyl alcohol and sodium lauryl sulphate, such as approximately 80 wt. % based on the combined amount of cetearyl alcohol and sodium lauryl sulphate.

When the hair conditioner concentrate is a combination of cetearyl alcohol and sodium lauryl sulphate, the sodium lauryl sulphate may be present in an amount of 5 to 40 wt. % based on the combined amount of cetearyl alcohol and sodium lauryl sulphate, such as from 10 to 30 wt. % based on the combined amount of cetearyl alcohol and sodium lauryl sulphate, such as from 15 to 25 wt. % based on the combined amount of cetearyl alcohol and sodium lauryl sulphate, such as approximately 20 wt. % based on the combined amount of cetearyl alcohol and sodium lauryl sulphate.

Carbon Dioxide Effervescing System

As discussed herein, the present invention contains a carbon dioxide effervescing system comprising a salt of carbonic acid and an acidifying agent. In one aspect the present invention contains a carbon dioxide effervescing system consisting of or consisting essentially of a salt of carbonic acid and an acidifying agent.

The carbon dioxide effervescing system may be present in any suitable amount to achieve the required dispersion of the hair conditioner concentrate. In one aspect the carbon dioxide effervescing system is present in an amount of at least 3% by weight of the solid hair conditioner composition. In one aspect the carbon dioxide effervescing system is present in an amount of at least 4% by weight of the solid hair conditioner composition. In one aspect the carbon dioxide effervescing system is present in an amount of at least 5% by weight of the solid hair conditioner composition. In one aspect the carbon dioxide effervescing system is present in an amount of at least 6% by weight of the solid hair conditioner composition. In one aspect the carbon dioxide effervescing system is present in an amount of at least 7% by weight of the solid hair conditioner composition. In one aspect the carbon dioxide effervescing system is present in an amount of at least 8% by weight of the solid hair conditioner composition. In one aspect the carbon dioxide effervescing system is present in an amount of at least 9% by weight of the solid hair conditioner composition.

In one aspect the carbon dioxide effervescing system is present in an amount of no greater than 25% by weight of the solid hair conditioner composition. In one aspect the carbon dioxide effervescing system is present in an amount of no greater than 20% by weight of the solid hair conditioner composition. In one aspect the carbon dioxide effervescing system is present in an amount of no greater than 15% by weight of the solid hair conditioner composition. In one aspect the carbon dioxide effervescing system is present in an amount of no greater than 10% by weight of the solid hair conditioner composition.

In one aspect the carbon dioxide effervescing system is present in an amount of from 3 to 25% by weight of the solid hair conditioner composition. In one aspect the carbon dioxide effervescing system is present in an amount of from 5 to 25% by weight of the solid hair conditioner composition. In one aspect the carbon dioxide effervescing system is present in an amount of from 6 to 20% by weight of the solid hair conditioner composition. In one aspect the carbon dioxide effervescing system is present in an amount of from 6 to 15% by weight of the solid hair conditioner composition. In one aspect the carbon dioxide effervescing system is present in an amount of from 6 to 10% by weight of the solid hair conditioner composition.

The components of the carbon dioxide generating system may be present in any suitable amount relative to each other. In one aspect the salt of carbonic acid and the acidifying agent are present in a weight ratio of from 90:10 to 50:50. In one aspect the salt of carbonic acid and the acidifying agent are present in a weight ratio of from 90:10 to 70:30.

The salt of carbonic acid may be any suitable salt. In one aspect the salt of carbonic acid is selected from alkali metal carbonates, alkali metal bicarbonates and mixtures thereof. In one aspect the salt of carbonic acid is selected from sodium bicarbonate, sodium carbonate and mixtures thereof. In one aspect the salt of carbonic acid is sodium bicarbonate.

The acidifying agent may be selected from all suitable acidifying agents. In one aspect the acidifying agent is selected from monocarboxylic acids, dicarboxylic acids, tricarboxylic acids and mixtures thereof. In one aspect the acidifying agent is selected citric acid, potassium bitartrate (cream of tartar) and mixtures thereof. In one aspect the acidifying agent is citric acid.

In one aspect the salt of carbonic acid is sodium bicarbonate and the acidifying agent is citric acid.

In one aspect the salt of carbonic acid is sodium bicarbonate and the acidifying agent is citric acid present in a weight ratio of from 90:10 to 50:50, preferably from 90:10 to 70:30, wherein the sodium bicarbonate and the citric acid are present in an combined amount of from 3 to 25%, preferably 5 to 25%, preferably 5 to 20%, preferably 6 to 20%, preferably 6 to 15%, preferably 6 to 10%, by weight of the solid hair conditioner composition.

Vegetable Oil, Vegetable Butter, Wax or Mixtures Thereof

The solid hair conditioner composition of the present invention may contain vegetable oil, vegetable butter, wax or mixture thereof. In one aspect the solid hair conditioner composition contains vegetable oil. In one aspect the solid hair conditioner composition contains vegetable butter. In one aspect the solid hair conditioner composition contains vegetable oil and vegetable butter. The vegetable oil, vegetable butter, wax or mixture thereof may be present in any suitable amount to provide the necessary properties of the final product. In one preferred aspect the vegetable oil, vegetable butter and wax are present in a total amount of from 5 to 35% by weight of the solid hair conditioner composition, such as in a total amount of from 10 to 25% by weight of the solid hair conditioner composition.

It will be understood by one skilled in the art that the wax referred to in this section is in addition to any emulsifying wax of the hair conditioner concentrate. Therefore in one aspect the solid hair conditioner composition of the present invention comprises a wax and a hair conditioner concentrate comprising an emulsifying wax wherein the wax and the emulsifying wax are different.

The vegetable oil, vegetable butter and wax may be selected from any materials suitable to achieve the purpose of the present invention. In one preferred aspect, the vegetable oil, vegetable butter and wax are selected from cocoa butter, murumuru butter, cupuacu butter, illipe butter, mango butter, sesame oil, rosehip oil, almond oil, raspberry seed oil, beeswax, rapeseed wax, japan wax and mixtures thereof.

In one preferred aspect the vegetable oil, vegetable butter, wax or mixture thereof is vegetable oil. In one preferred aspect the vegetable oil is selected from jojoba oil, almond oil, avocado oil, castor oil, moringa oil, olive oil and mixtures thereof.

The oils, butters and waxes that may be incorporated into the composition may be selected by one skilled in the art based on their suitability and the type of hair to be treated with the hair conditioner. Some details of the oils and the hair types which they are used are as follows:

Olive oil—used in all the formulation as it is the only oil proven to improve the elastic strength of the hair. It helps the cuticle and the cortex of the hair stretch.

Jojoba oil—used as it is a liquid wax, resulting in a dry finish when used on the hair and tends to improve the condition of dry and fine hair.

Almond Oil—softens and adds shine to the hair. Suitable for all hair types.

Avocado Oil—adds strength and shine to the hair. Suitable for all hair types.

Lanolin—resembles the hair's sebum. It is an excellent emollient and an effective moisturiser. It coats and protects the hair, making it a very effective conditioner of dry hair.

Castor Oil—rich oil, to protect the hair but also adds strength and shine. Suitable for dry and damaged hair.

Cationic Surfactant

The solid hair conditioner composition of the present invention may further comprise at least one cationic surfactant. The cationic surfactant may be present in any suitable amount to provide the necessary properties of the final product. The solid hair conditioner composition may contain cationic surfactant in an amount of at least 3% by weight of the solid hair conditioner composition. The solid hair conditioner composition may contain cationic surfactant in an amount of at least 5% by weight of the solid hair conditioner composition. The solid hair conditioner composition may contain cationic surfactant in an amount of at no greater than 20% by weight of the solid hair conditioner composition. The solid hair conditioner composition may contain cationic surfactant in an amount of at no greater than 15% by weight of the solid hair conditioner composition. The solid hair conditioner composition may contain cationic surfactant in an amount of at no greater than 10% by weight of the solid hair conditioner composition.

In one aspect the cationic surfactant is present in an amount of from 5 to 20% by weight of the solid hair conditioner composition. In one aspect the cationic surfactant is present in an amount of from 5 to 10% by weight of the solid hair conditioner composition.

The cationic surfactant may be selected from any suitable cationic surfactant. In one aspect the cationic surfactant is selected from cationic guar gum, behenyl trimethyl ammonium chloride, polyquaternium-81, cetrimonium bromide and mixtures thereof. In one aspect the cationic surfactant is behenyl trimethyl ammonium chloride.

In one preferred aspect the cationic surfactant is cationic guar gum. Guar gum refers to the mucilage present in the seed of the *Cyamopsis tetragonoloba* plant, and is widely known for its industrial applications as a thickening, stabilising and dietary additive. The use of guar gum in the present invention may be advantageous as it produces a viscous pseudoplastic solution that enables the effective suspension of active ingredients and other additives when dissolved and dispersed within water. Furthermore, due to the inherent low-shear viscosity of guar gum solutions, the composition of the present invention can be readily applied to the hair, coating the individual hair shafts and allowing the active ingredients to condition the cuticle, without any loss of structural cohesion or integrity of the composition on the hair.

A preferred solid hair conditioner of the present invention comprises (i) a hair conditioner concentrate in an amount of from 40 to 70% by weight of the solid hair conditioner composition, wherein the hair conditioner concentrate is a combination of cetearyl alcohol and sodium lauryl sulphate (SLS) present in a ratio of from 20:1 to 5:1 by weight.

(ii) a carbon dioxide effervescing system comprising sodium bicarbonate and citric acid in a weight ratio of from 90:10 to 50:50, wherein the carbon dioxide effervescing system is present in an amount of from 3 to 25% by weight of the solid hair conditioner composition;

(iii) jojoba oil, almond oil, avocado oil, castor oil, moringa oil, olive oil, lanolin or a mixture thereof, present in a total amount of from 5 to 35% by weight of the solid hair conditioner composition.

(iv) at least one cationic surfactant selected from cationic guar gum, behenyl trimethyl ammonium chloride, polyquaternium-81, cetrimonium bromide and mixtures thereof, wherein the cationic surfactant is present in an amount of from 5 to 20% by weight of the solid hair conditioner composition.

A preferred solid hair conditioner of the present invention comprises (i) a hair conditioner concentrate in an amount of from 40 to 70% by weight of the solid hair conditioner composition, wherein the hair conditioner concentrate is a combination of cetearyl alcohol and sodium lauryl sulphate (SLS) present in a ratio of from 20:1 to 5:1 by weight.

(ii) a carbon dioxide effervescing system comprising sodium bicarbonate and citric acid in a weight ratio of from 90:10 to 50:50, wherein the carbon dioxide effervescing system is present in an amount of from 3 to 25% by weight of the solid hair conditioner composition;

(iii) jojoba oil, almond oil, avocado oil, castor oil, moringa oil, olive oil, lanolin or a mixture thereof, present in a total amount of from 5 to 35% by weight of the solid hair conditioner composition.

(iv) cationic guar gum in an amount of from 5 to 20% by weight of the solid hair conditioner composition.

Unit Dose

As discussed herein, we have found that by providing the present system a user may make a freshly prepared batch of hair conditioner, for example in the manner in which it is prepared in a hair salon. This may be done with minimal experience and creating minimal mess. To further simplify the preparation of the product, in one aspect the composition is provided as a unit dose. To prepare their conditioner, this unit dose may be combined with the necessary amount of water. Yet further we have found that the easy preparation may be improved by embedding a stirring device in the unit dose of solid hair conditioner. By this means, the solid hair conditioner composition may be placed in water and as it begins to disperse the stirring device may be used to agitate the water and further disperse the solid hair conditioner. Once the solid hair conditioner has completely disintegrated such that the stirrer is no longer embedded within it, the stirrer may be used to further mix the dispersed hair conditioner. The provision of a unit dose is also advantageous because it allows for the preparation of enough hair conditioner for one application so waste product is not created.

We have identified that this concept of providing a solid cosmetic product into which a stirring device has been embedded may be applied in other cosmetic applications.

Therefore, in a further aspect there is provided a unit dose of a solid cosmetic composition, wherein the unit dose comprises (a) a solid hair conditioner composition in a predetermined amount (b) a stirring device for stirring a liquid wherein the stirring device is partially embedded within the solid cosmetic composition.

To further simplify the preparation of the composition, preferably the unit dose denotes the amount of liquid into which the predetermined amount of solid hair conditioner composition should be dispersed in use. This may be simply done by marking the amount of liquid on the stirrer. For example the stirrer may be a wooden implement such as a spoon onto which is marked the amount of liquid into which the solid unit dose is to be combined.

The stirring device may be any suitable stirrer such as a spatula, fork, spoon or other utensil. The stirring device may be made from any suitable material such wood, metal, plastic or combinations thereof.

Further Components

The solid hair conditioner composition may contain one or more additional components such as to provide the desired composition. In one aspect the solid hair conditioner composition further comprising at least one additional component selected from humectants, surfactants, fruits, vegetables, herbs, seaweeds, cereals, beans, proteins, binders, fillers, dispersants, opacifiers, perfumes, colours, fragrances and mixtures thereof. In one aspect, the solid hair conditioner composition comprising a further component selected from binders, fillers, fruits, vegetables, humectants, dispersants and mixtures thereof.

In one aspect the solid hair conditioner composition contains one or more fragrances. Preferably the solid hair conditioner composition comprises fragrance in an amount of no greater than 6% by weight of the solid cosmetic composition. Preferably the solid hair conditioner composition comprises fragrance in an amount of no greater than 5% by weight of the solid cosmetic composition. If present, fragrance may be present in an amount of from 0.01 to 6% by weight of the total composition. If present, fragrance may be present in an amount of from 0.01 to 5% by weight of the total composition. The amount of fragrances is preferably from 0.1% to 5% by weight of the total composition, such as from 0.1% to 4% by weight of the total composition, such as from 0.5% to 5% by weight of the total composition, such as from 1% to 5% by weight of the total composition, such as from 0.5% to 4% by weight of the total composition, such as from 0.5% to 3% by weight of the total composition, such as from 0.5% to 2.5% by weight of the total composition, such as from 1.5% to 2.5% by weight of the total composition. Alternatively, in one aspect, the solid hair conditioner composition is fragrance free.

The essential oils may be selected based on the fragrance desired, skin type to be treated and other effects desired based on the well-known properties of essential oils. The addition of essential oils, when taken in to the nose, is known to alter mood. For example, essential oils are known to create effects of drowsiness or stimulating the senses. Many effects can be achieved by the use of essential oils.

In one embodiment, the one or more essential oils present in the product are selected from Rosewood, Sandalwood, Chamomile, Eucalyptus, Tonka absolute, Lemon myrtle, Jasmin, Ylang ylang, Labdanum, Lemongrass, Rose Absolute, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the product are selected from Rosewood, Sandalwood, Chamomile, Eucalyptus, Lavender, Tonka absolute, Rose absolute.

Vitamins, particularly B, C and E are very beneficial for the hair and scalp. Vitamin rich ingredients such as Wheatgerm oil can also be used to deliver vitamins on to the hair and scalp. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the product of a material, such as a natural material, that has a high vitamin content.

In one aspect the solid hair conditioner composition further comprises a colorant material. If present, colorant materials may be present in an amount of from 0.001 to 3% by weight of the total composition.

In one aspect the solid hair conditioner composition contains a humectant. In one aspect, the humectant is selected from honey, glycerine, sorbitol, agave nectar, fruit syrups, herbal syrups and mixtures thereof. Preferably the humectant is selected from honey, glycerine, sorbitol and mixtures thereof.

In one aspect the solid hair conditioner composition contains water. In one aspect the solid hair conditioner composition is free or substantially free of water. Preferably the solid hair conditioner composition comprises water in an amount of no greater than 5% by weight of the solid cosmetic composition, such as in an amount of no greater than 4% by weight of the solid cosmetic composition, such as in an amount of no greater than 3% by weight of the solid cosmetic composition, such as in an amount of no greater than 2% by weight of the solid cosmetic composition, such as in an amount of no greater than 1% by weight of the solid cosmetic composition, such as in an amount of no greater than 0.5% by weight of the solid cosmetic composition, such as in an amount of no greater than 0.1% by weight of the solid cosmetic composition, such as in an amount of no greater than 0.01% by weight of the solid cosmetic composition.

In one aspect the solid hair conditioner composition contains preservatives. In one aspect the solid hair conditioner composition is free or substantially free of preservatives. Preferably the solid hair conditioner composition comprises preservatives in an amount of no greater than 5% by weight of the solid cosmetic composition, such as in an amount of no greater than 4% by weight of the solid cosmetic composition, such as in an amount of no greater than 3% by weight of the solid cosmetic composition, such as in an amount of no greater than 2% by weight of the solid cosmetic composition, such as in an amount of no greater than 1% by weight of the solid cosmetic composition, such as in an amount of no greater than 0.5% by weight of the solid cosmetic composition, such as in an amount of no greater than 0.1% by weight of the solid cosmetic composition, such as in an amount of no greater than 0.01% by weight of the solid cosmetic composition.

An advantage of the solid hair conditioner composition of the present invention is that it does not require packaging. Thus preferably the solid hair conditioner composition is provided free of packaging. It will be understood that the product may include labelling providing information on the composition of the product and/or its usage. The primary purpose of such labelling is to carry information rather than to pack the product.

Use

To use the product of the present invention, the end user will typically place the product in a container. A small amount of warm or hot water can then be added to the container, typically to just cover the solid product. The product will start to disperse and effervesce. Once a significant amount of product has dispersed more water can be added and the product gently stirred. Water can then be added until the desired consistency of dispersed product has been formed. This consistency may be determined by the user based on, for example, their preference or their hair type or condition.

In one aspect the product is dispersed in a predetermined amount of water. In one aspect the unit dose of the present invention is dispersed in from 200 to 750 ml of water, such as from 200 to 500 ml of water, such as from 250 to 500 ml of water, such as approximately 250 ml of water.

EXAMPLE

The invention will now be described with reference to the following non-limiting example.

| Formula % | Raw Material Type | Batch Size: (g) |
|---|---|---|
| 55.00 | Cetearyl Alcohol & SLS | 110.00 |
| 9.00 | Sodium Bicarbonate | 18.00 |
| 2.00 | Olive Oil | 4.00 |
| 18.00 | Almond Oil | 36.00 |
| 8.00 | Bimethyl Trimethyl Ammonium Chloride | 16.00 |
| 4.00 | Fragrance | 8.00 |
| 4.00 | Citric Acid | 8.00 |
| 100.00 | | 200.00 |

Method:
1. The emulsifying wax is warmed (to a temperature in the range of 60° C.-90° C., with 65° C. being the ideal temperature) to melt.
2. The oils, butter and other waxes are then added to the wax when the temperature falls within the range of 45° C.-70° C., with 50° C. being the ideal temperature.
3. The cationic surfactant is stirred through the oil phase, once the oil phase has reached a temperature of between 35° C.-55° C., with the ideal temperature being between 45° C.
4. When the temperature reaches below 35° C., the sodium bicarbonate can be added and stirred thoroughly through the product, along with any fragrance material, colourant or other desired materials. The citric acid can then be added and stirred thoroughly through the product.
5. The product is then poured into moulds and a stirring device is added and cooled to between 4° C.-10° C. to set, with the ideal temperature being 8° C.
6. Once set the product is removed and is ready to use.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:
1. A solid hair conditioner composition comprising
(i) a hair conditioner concentrate in an amount of at least 20% by weight of the solid hair conditioner composition, wherein the hair condition concentrate is selected from the group consisting of emulsifying waxes, sodium polynaphthalene sulfonate, stearamidopropyl dimethylamine and mixtures thereof;
(ii) a carbon dioxide effervescing system comprising a salt of carbonic acid and an acidifying agent; and
(iii) cationic guar gum;
wherein the salt of carbonic acid and the acidifying agent are present in a weight ratio of 70:30 to 90:10.

2. A solid hair conditioner composition according to claim 1 wherein the hair conditioner concentrate is present in an amount of from 40 to 70% by weight of the solid hair conditioner composition.

3. A solid hair conditioner composition according to claim 1 wherein the hair conditioner concentrate is present in an amount of from 50 to 65% by weight of the solid hair conditioner composition.

4. A solid hair conditioner composition according to claim 1, wherein the hair conditioner concentrate is selected from emulsifying waxes.

5. A solid hair conditioner composition according to claim 4 wherein the emulsifying wax is a combination of cetearyl alcohol and sodium lauryl sulphate (SLS).

6. A solid hair conditioner composition according to claim 5 wherein the cetearyl alcohol and sodium lauryl sulphate are present in a ratio of from 20:1 to 2:1 by weight.

7. A solid hair conditioner composition according to claim 5 wherein the cetearyl alcohol and sodium lauryl sulphate are present in a ratio of from 12:1 to 4:1 by weight.

8. A solid hair conditioner composition according to claim 1, wherein the carbon dioxide effervescing system is present in an amount of from 3 to 25% by weight of the solid hair conditioner composition.

9. A solid hair conditioner composition according to claim 1, wherein the carbon dioxide effervescing system is present in an amount of from 6 to 20% by weight of the solid hair conditioner composition.

10. A solid hair conditioner composition according to claim 1, wherein the salt of carbonic acid is selected from alkali metal carbonates, alkali metal bicarbonates and mixtures thereof.

11. A solid hair conditioner composition according to claim 1, wherein the salt of carbonic acid is selected from sodium bicarbonate, sodium carbonate and mixtures thereof.

12. A solid hair conditioner composition according to claim 1, wherein the acidifying agent is selected from monocarboxylic acids, dicarboxylic acids, tricarboxylic acids and mixtures thereof.

13. A solid hair conditioner composition according to claim 1, wherein the acidifying agent is selected citric acid, potassium bitartrate and mixtures thereof.

14. A solid hair conditioner composition according to claim 1 further comprising vegetable oil, vegetable butter, wax or a mixture thereof.

15. A solid hair conditioner composition according to claim 14 wherein vegetable oil, vegetable butter and wax are present in a total amount of from 5 to 35% by weight of the solid hair conditioner composition.

16. A solid hair conditioner composition according to claim 14 wherein vegetable oil, vegetable butter and wax are present in a total amount of from 10 to 25% by weight of the solid hair conditioner composition.

17. A solid hair conditioner composition according to claim 14, wherein the vegetable oil, vegetable butter, wax or mixture thereof is vegetable oil.

18. A solid hair conditioner composition according to claim 14, wherein the vegetable oil is selected from jojoba oil, almond oil, avocado oil, castor oil, moringa oil, olive oil and mixtures thereof.

19. A solid hair conditioner composition according to claim 14 wherein the wax is selected from beeswax, Japan wax, rapeseed wax, candelilla wax, lanolin and mixtures thereof.

20. A solid hair conditioner composition according to claim 1 wherein the cationic guar gum is present in an amount of from 5 to 20% by weight of the solid hair conditioner composition.

21. A solid hair conditioner composition according to claim 1 wherein the cationic guar gum is present in an amount of from 5 to 10% by weight of the solid hair conditioner composition.

22. A solid hair conditioner composition according to claim 1 comprising
- (i) a hair conditioner concentrate in an amount of from 40 to 70% by weight of the solid hair conditioner composition, wherein the hair conditioner concentrate is a combination of cetearyl alcohol and sodium lauryl sulphate (SLS) present in a ratio of from 20:1 to 2:1 by weight,
- (ii) a carbon dioxide effervescing system comprising sodium bicarbonate and citric acid in a weight ratio of from 70:30 to 90:10 to 50:50, wherein the carbon dioxide effervescing system is present in an amount of from 5 to 25% by weight of the solid hair conditioner composition;
- (iii) jojoba oil, almond oil, avocado oil, castor oil, moringa oil, olive oil, lanolin or a mixture thereof, present in a total amount of from 5 to 35% by weight of the solid hair conditioner composition,
- (iv) cationic guar gum in an amount of from 5 to 20% by weight of the solid hair conditioner composition.

* * * * *